(12) United States Patent
Gazeau (10) Patent No.: US 7,285,244 B2
(45) Date of Patent: Oct. 23, 2007

(54) AUTOMATED DEVICE FOR BIOLOGICAL ANALYSIS

(75) Inventor: Michel Gazeau, Saint-Julien-en-Genevois (FR)

(73) Assignee: Genomic S.A. (FR)

( * ) Notice: Subject to any disclaimer, the term of this patent is extended or adjusted under 35 U.S.C. 154(b) by 565 days.

(21) Appl. No.: 10/236,530

(22) Filed: Sep. 6, 2002

(65) Prior Publication Data

US 2003/0059341 A1    Mar. 27, 2003

Related U.S. Application Data

(63) Continuation of application No. PCT/FR01/00758, filed on Mar. 9, 2001.

(30) Foreign Application Priority Data

Mar. 9, 2000    (FR) .................................. 00 03137

(51) Int. Cl.
*G01N 22/00* (2006.01)
(52) U.S. Cl. .................. 422/64; 422/63; 422/65; 422/99; 422/100; 422/101; 436/180
(58) Field of Classification Search .......... 422/63–65, 422/104, 99–101; 436/46, 180
See application file for complete search history.

(56) References Cited

U.S. PATENT DOCUMENTS

| 4,314,523 A | 2/1982 | Boeckel et al. |
| 4,468,410 A | 8/1984 | Zeya |
| 4,701,157 A * | 10/1987 | Potter .......................... 494/16 |
| 4,853,188 A | 8/1989 | Toya |
| 5,304,355 A * | 4/1994 | Yant et al. .................. 422/225 |
| 5,589,400 A | 12/1996 | Hayes |
| 5,795,061 A * | 8/1998 | Perlman ..................... 366/130 |
| 6,027,617 A * | 2/2000 | Hayashi et al. ............. 204/170 |

FOREIGN PATENT DOCUMENTS

| EP | 0047189 | 7/1985 |
| EP | 0947819 | 10/1999 |
| EP | 0984263 | 3/2000 |

* cited by examiner

*Primary Examiner*—Jill Warden
*Assistant Examiner*—Jyoti Nagpaul
(74) *Attorney, Agent, or Firm*—DLA Piper US LLP (57) ABSTRACT

An automated device for biological analysis including a rotatable rotor, and at least one reactor supported on the rotor and including an agitator composed of a blade which can either be 1) supported on a lower portion of a biochip carrier formed at an angle to retain a small volume of liquid, or to apply the liquid on a biochip on the biochip carrier such that liquid spreads over a surface of the biochip and without forming an air bubble of the volume of liquid retained, or 2) enter completely into a body portion of the reactor to allow sliding of the biochip carrier.

14 Claims, 11 Drawing Sheets

AUTOMATED DEVICE FOR BIOLOGICAL ANALYSIS

RELATED APPLICATION

This is a continuation of International Application No. PCT/FR01/00758, with an international filing date of Mar. 9, 2001, which is based on French Patent Application No. 00/03137, filed Mar. 9, 2000.

FIELD OF THE INVENTION

This invention relates to an automated device adapted to process biochips without human intervention and acquire signals for their subsequent analysis.

BACKGROUND

Biochips enable parallel analysis of a very large number of molecules, essentially nucleic acids and proteins. The basic principle is recognition and pairing of two molecules that have affinities.

One of the collections of molecules is fixed in the form of minideposits or microdeposits on a solid support, fabric, glass slide, silicon chip, etc. The other molecule, which is labeled and generally in solution, is brought into contact with the samples deposited on the solid support. After an incubation period, the excess of labeled molecule is eliminated and the support is carefully washed. It is then necessary to detect and quantify the signal emitted by the molecules retained on the deposits. In certain cases, the retained molecule can be uncoupled from the deposits and a new molecule can be tested with the same solid support.

In order to process biochips, it is generally necessary to bring the deposits into contact with different reagents and then to wash them carefully. It is necessary to adjust the temperature of the reagents and the biochips. The most frequently employed tags are fluorescent, but other labeling techniques can be used.

The labeled molecule is a rare and/or expensive element. It is desirable to minimize the volume required. The other reagents, particularly the washing products, are not expensive and the reduction of the volumes used is much less important.

SUMMARY OF THE INVENTION

This invention relates to an automated device for biological analysis including a rotatable rotor, and at least one reactor supported on the rotor and including an agitator composed of a blade which can either be 1) supported on a lower portion of a biochip carrier formed at an angle to retain a small volume of liquid, or to apply the liquid on a biochip on the biochip carrier such that liquid spreads over a surface of the biochip and without forming an air bubble of the volume of liquid retained, or 2) enter completely into a body portion of the reactor to allow sliding of the biochip carrier.

DETAILED DESCRIPTION

It will be appreciated that the following description is intended to refer to specific embodiments of the invention selected for illustration in the drawings and is not intended to define or limit the invention, other than in the appended claims.

This invention pertains to an automated device capable of processing biochips without human intervention and of acquiring signals for their subsequent analysis. In addition to cost savings in terms of reagents, the automated device enables processing of a large number of biochips. The equipment is also relatively inexpensive because of its simplicity.

The heart of the device is a slow-speed centrifuge, the angular position of the rotor of which can be fixed in a precise manner by means, e.g., of a coder. The rotor, which can optionally be removable, is constituted by a hub on which are affixed spokes. Each spoke carries at its end a reactor which will be described below.

The cover of the centrifuge comprises various elements:

A number of fixed nozzles spaced apart in a substantially regular manner equal to the number of reactors of the rotor and located on a circumference whose radius is substantially equal to that of the center of the reactors to dispense liquid into the reactors. These nozzles are connected by calibrated catheters to the cover of a hermetic enclosure which comprises a number of tubes containing the labeled molecules. This enclosure can be subjected to a selected pressure for a selected period of time by means, e.g., of a gas carboy, which has the effect of flowing from the catheters to the reactors a substantially equal volume of the liquids contained in the tube. This enclosure can be cooled by any process to ensure good conservation of the labeled molecules.

A number of nozzles affixed on the cover between the preceding ones, connected to bottles under pressure or under reduced pressure, or to pumps, allows successive distribution in each reactor of the common reagents in large volume (on the order of several milliliters). Certain of these nozzles can discharge liquids for cleaning and decontamination of the device.

A mechanical translational movement device on a spoke makes it possible to pull to the periphery then to return to its initial position a gliding biochip-carrier part from each reactor or in other cases the reactors themselves, successively. This device can be constituted by a guided rack driven by a pinion substantially integral with a shaft of a fixed electric motor. A finger placed on the part located closest to the center of the mobile element can descend into the centrifuge and then rise again by means, e.g., of a cam. This finger enables the translational movement device to attach to the gliding part or the reactor.

The envelope of the centrifuge comprises an aperture which can be blocked by a part integral with the mechanical translational movement device and which allows passage of the biochip-carrier gliding part or the reactor. These latter parts are thus placed in the field of the signal-acquisition system. The envelope of the centrifuge can be equipped with one or more horizontal telescoping nozzles enabling injection of the reagent into each reactor or to suction out the reagents contained therein.

The shape of the bottom of the enclosure of the centrifuge is designed to allow complete evacuation of the reagents employed. The temperature inside the centrifuge is regulated. The rotation of the reactors at a very slow speed makes the temperature more uniform. If necessary, the hygrometry of the air in the enclosure can be controlled.

The bottom of the centrifuge and/or the interior of the cover can be equipped with a circular element of a form designed to cause movements of reactor parts.

Figure 1:
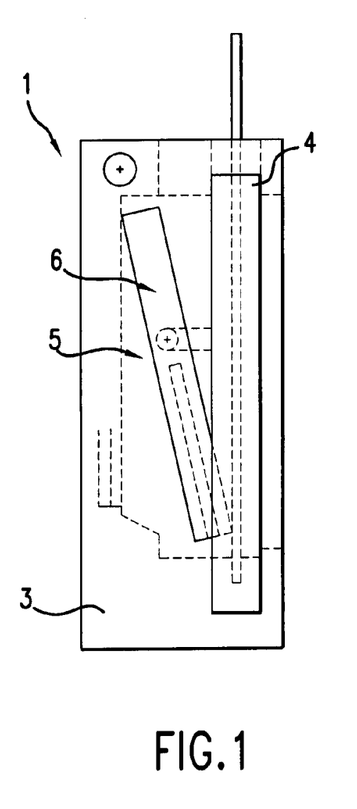
FIGS. 1, 2 and 3 illustrate a front view, a side view and a top view of a reactor in accordance with aspects of the invention, respectively.
Figure 2:
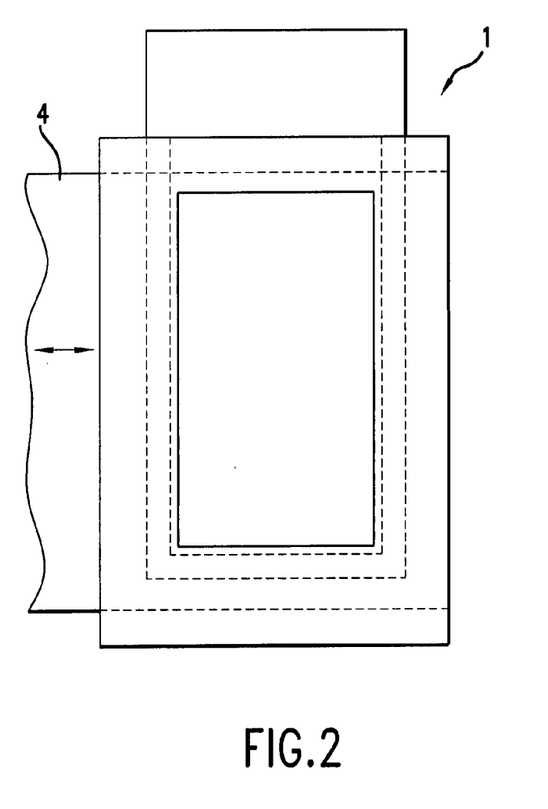
Figure 3:
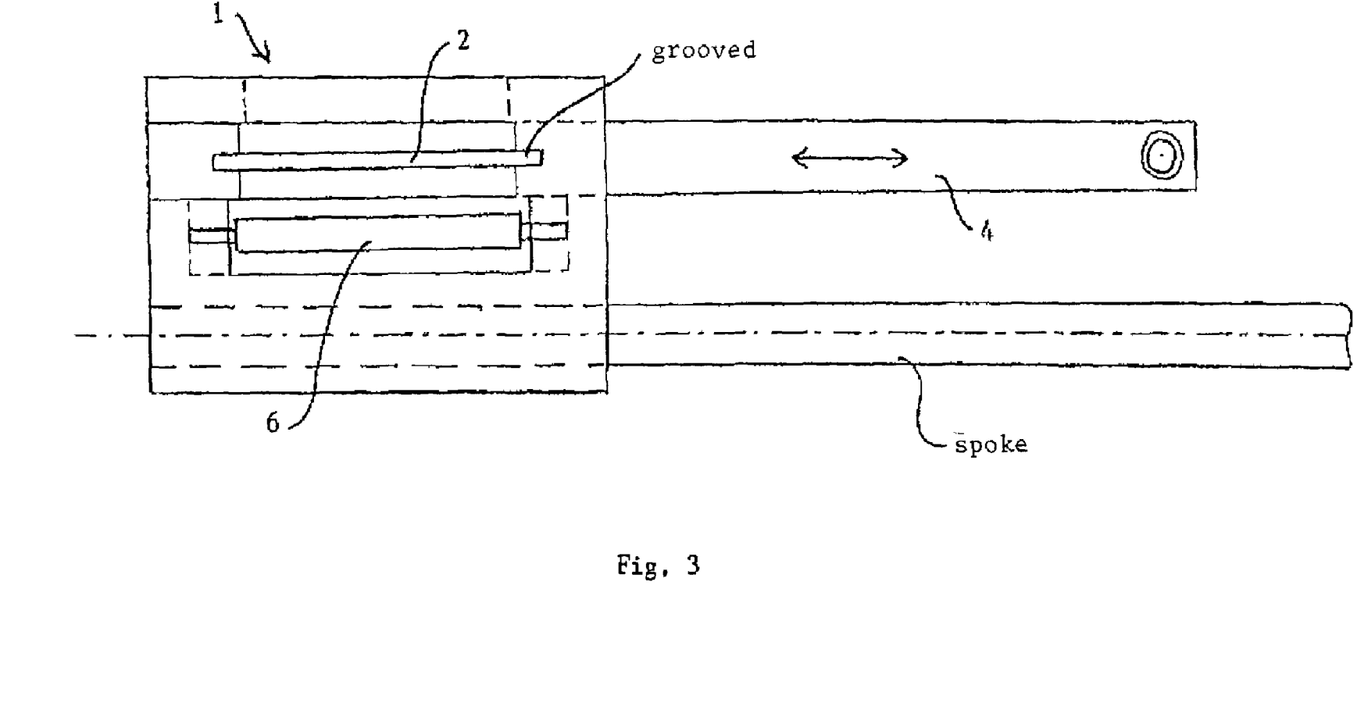
Figure 4:
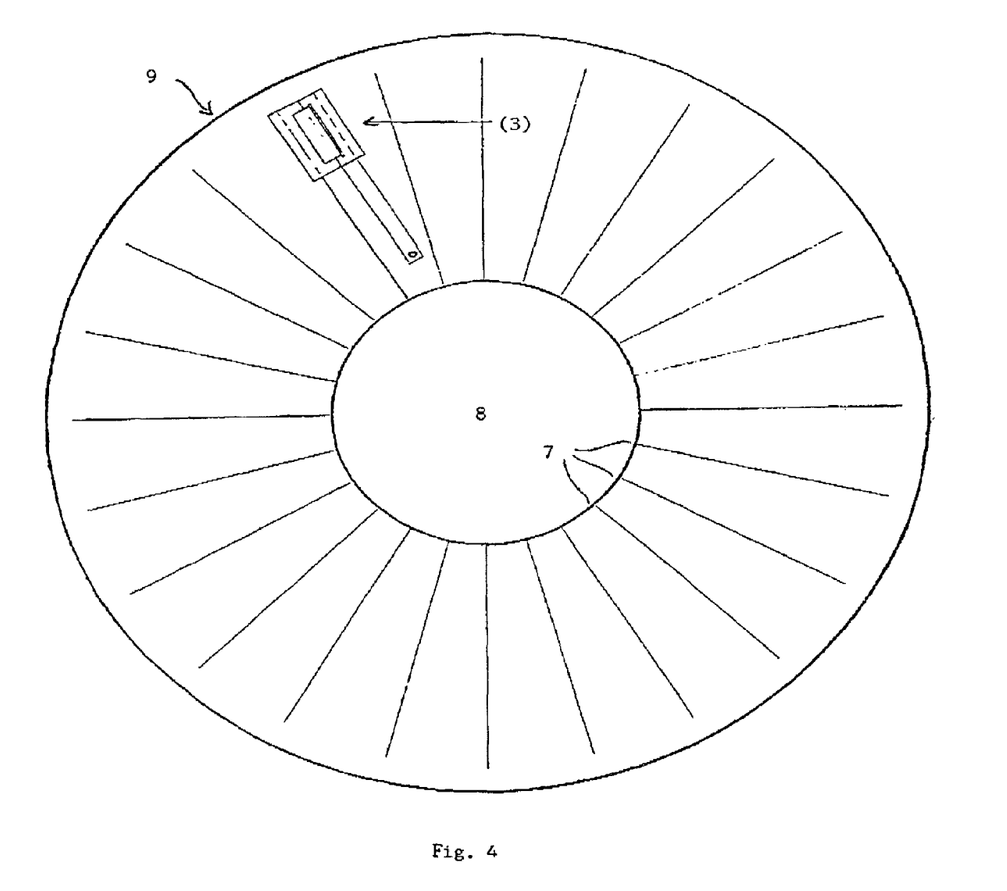
FIG. 4 illustrates a top view of a centrifuge in accordance with aspects of the invention.
Figure 5:
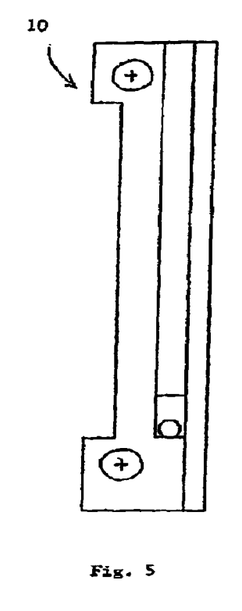
FIGS. 5 and 6 illustrate a side view and a front view of a centripetal valve carrier device in accordance with aspects of the invention, respectively.
Figure 6:
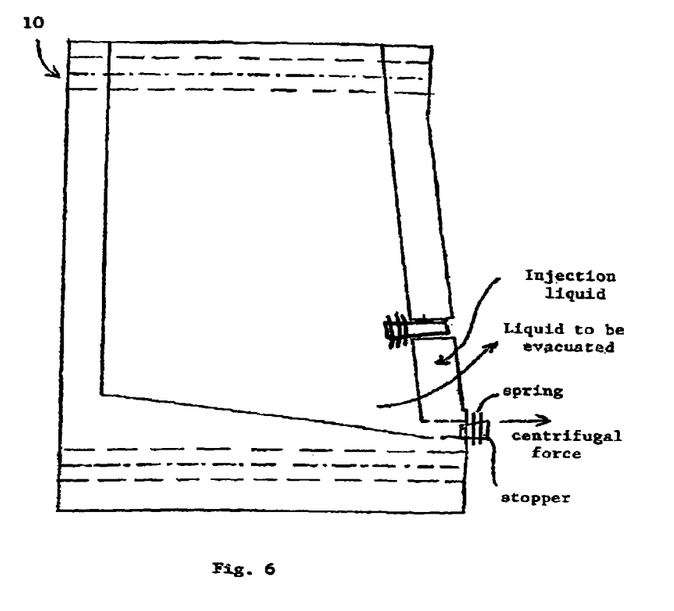
Figure 7:
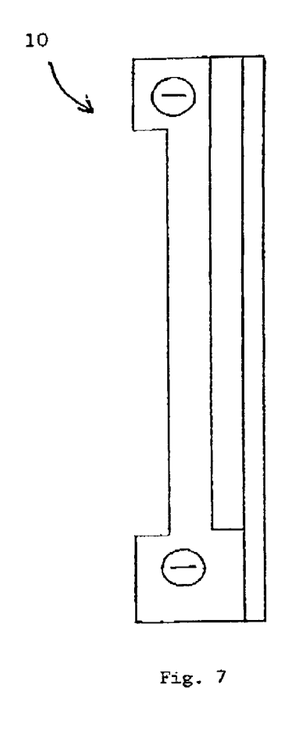
FIGS. 7, 8 and 9 illustrate a side view, a front view and a top view of a centrifuge drainage carrier device in accordance with aspects of the invention, respectively.
Figure 8:
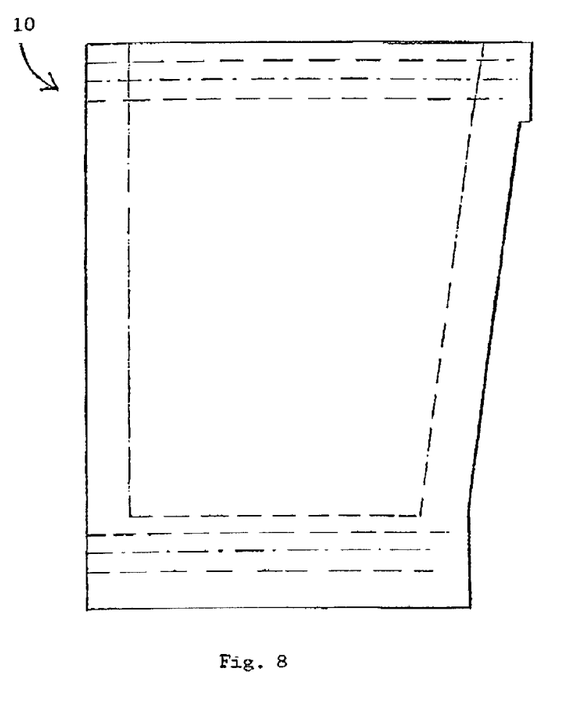
Figure 9:
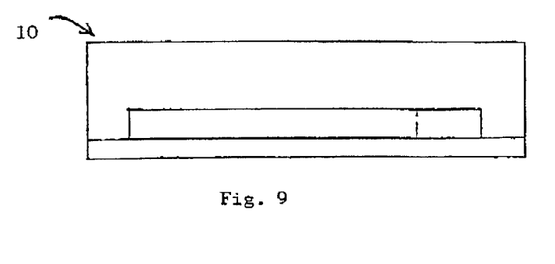
Figure 10:
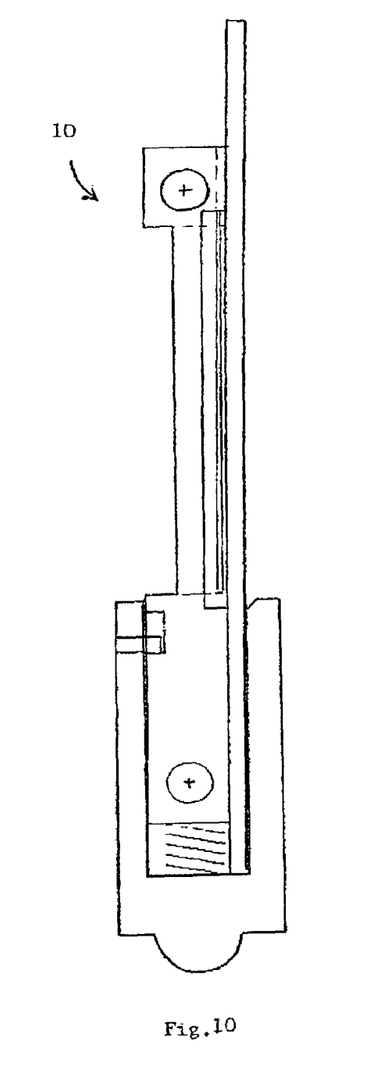
FIGS. 10 and 11 illustrate a side view and a front view of a capillary carrier device in accordance with aspects of the invention, respectively.
Figure 11:
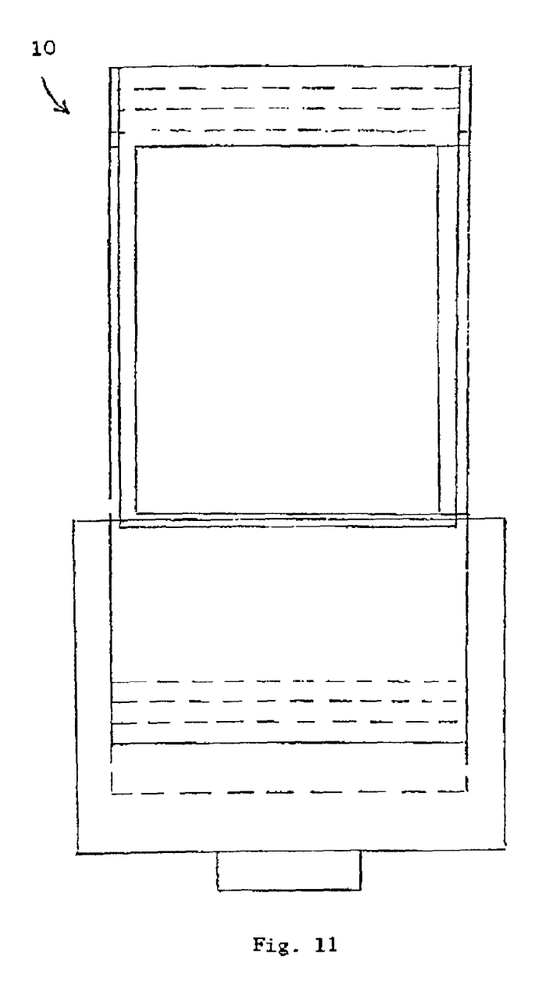
Figure 12:
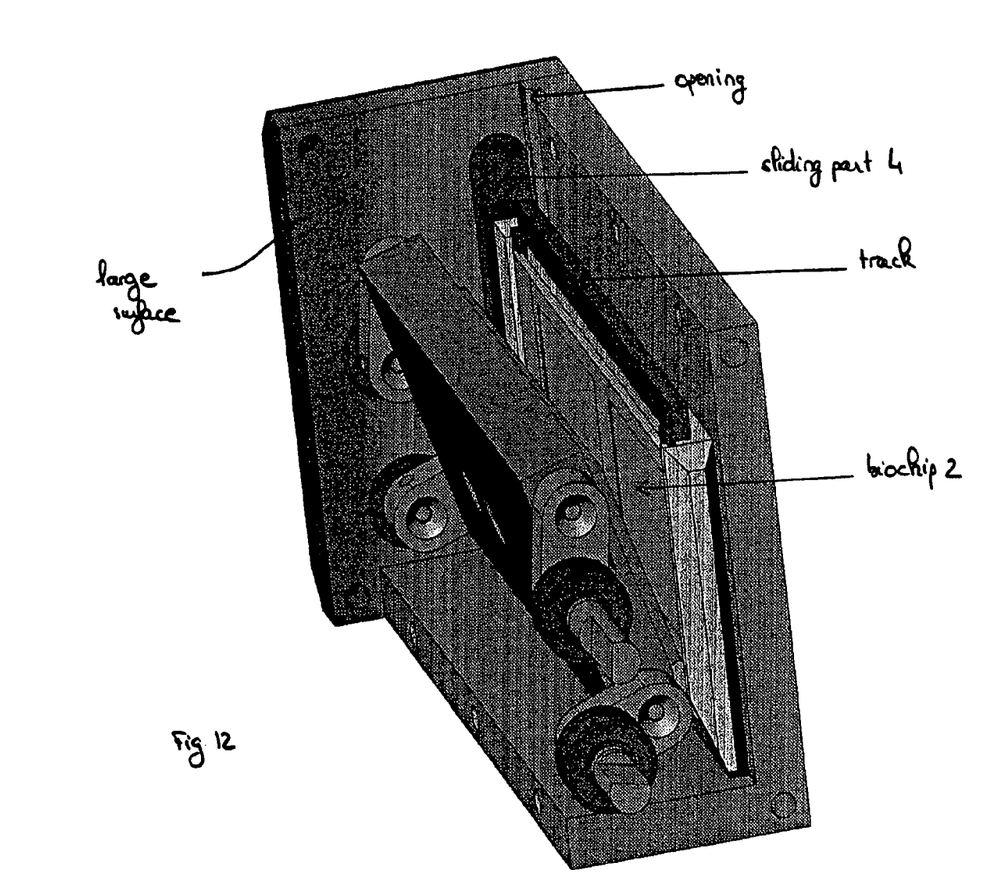
FIG. 12 is a perspective view of the apparatus shown in FIGS. 1 and 2.
Figure 13:
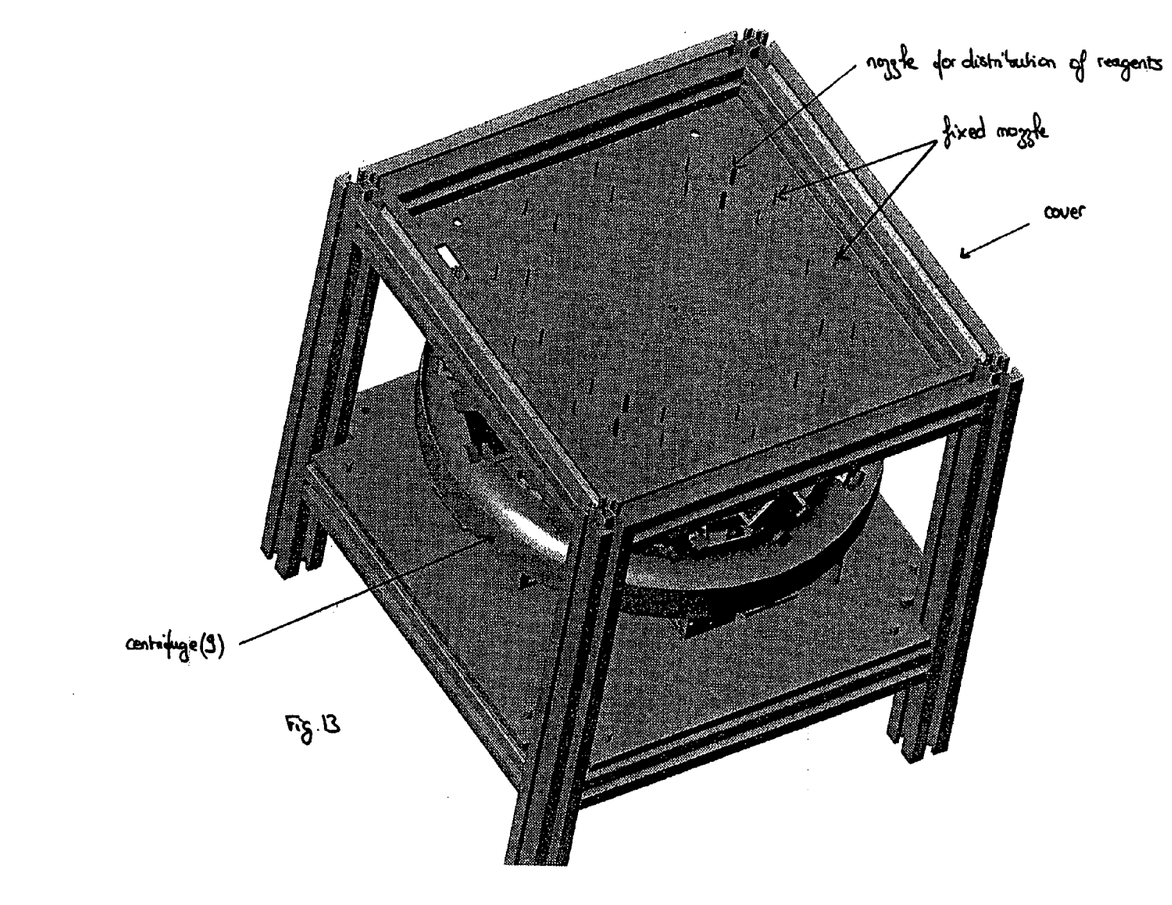
FIG. 13 is a perspective view of a cover and fixed nozzles of a reactor.
Figure 14:
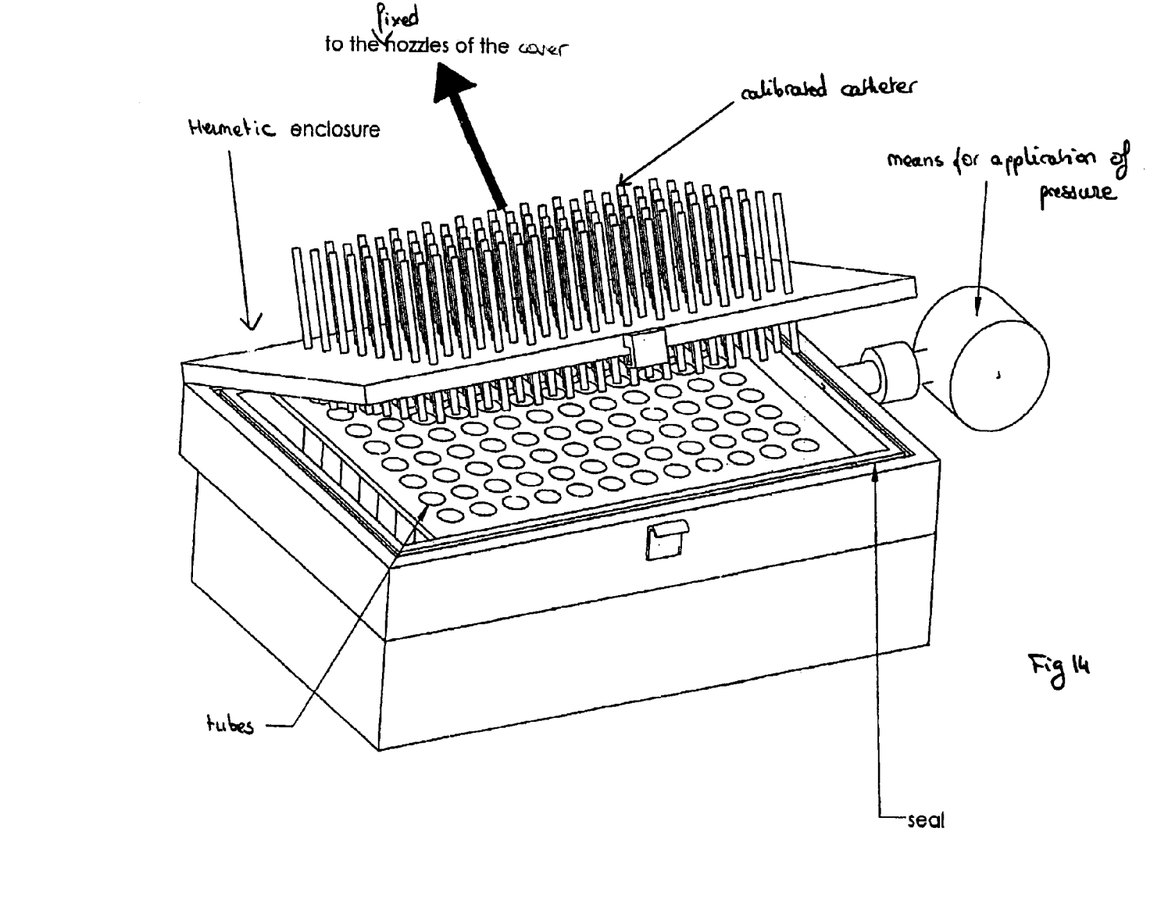
FIG. 14 is a perspective view of a hermetic enclosure.
Figure 15:
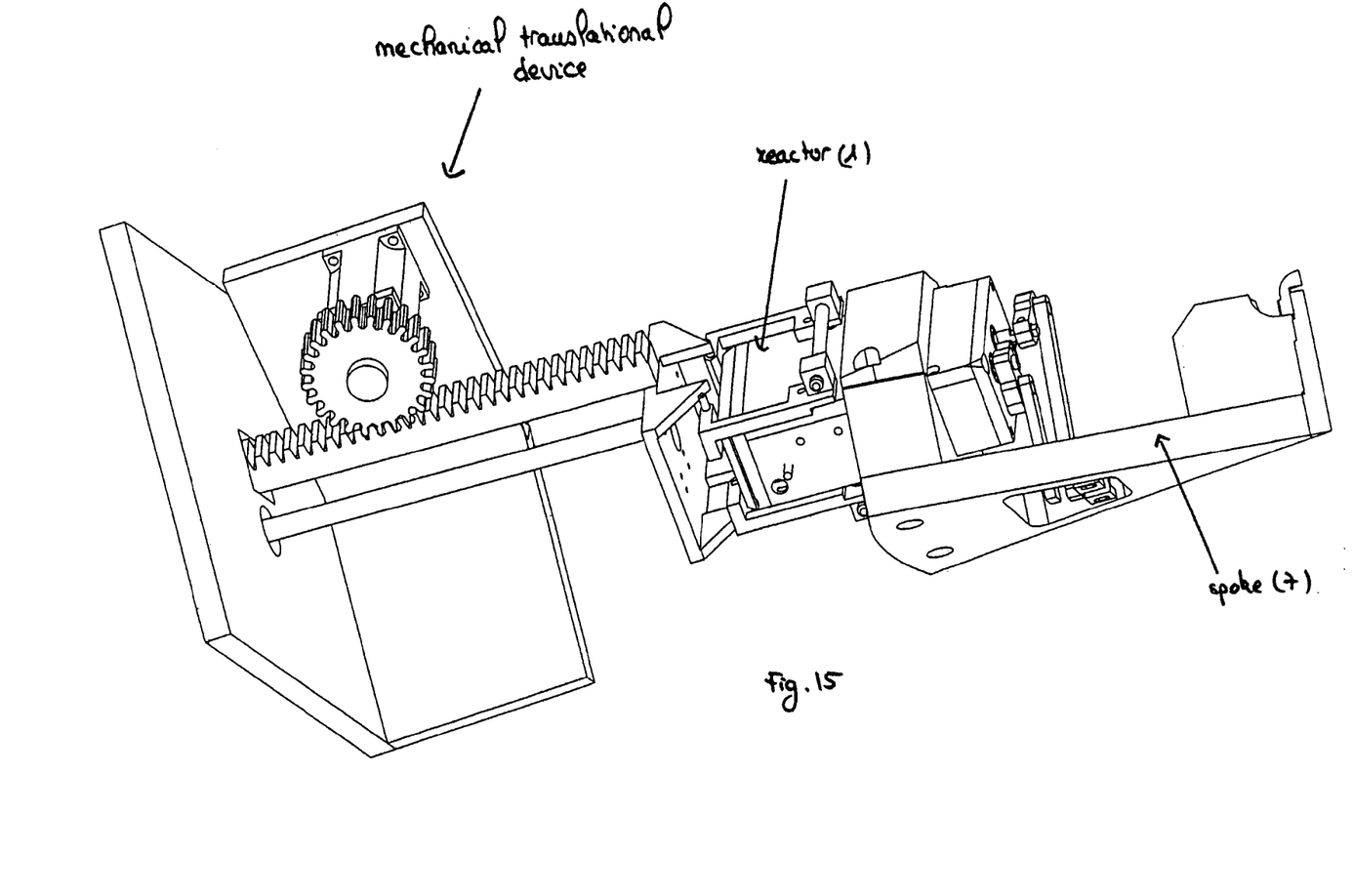
FIG. 15 is a perspective view of a mechanical translation device.
Figure 16:
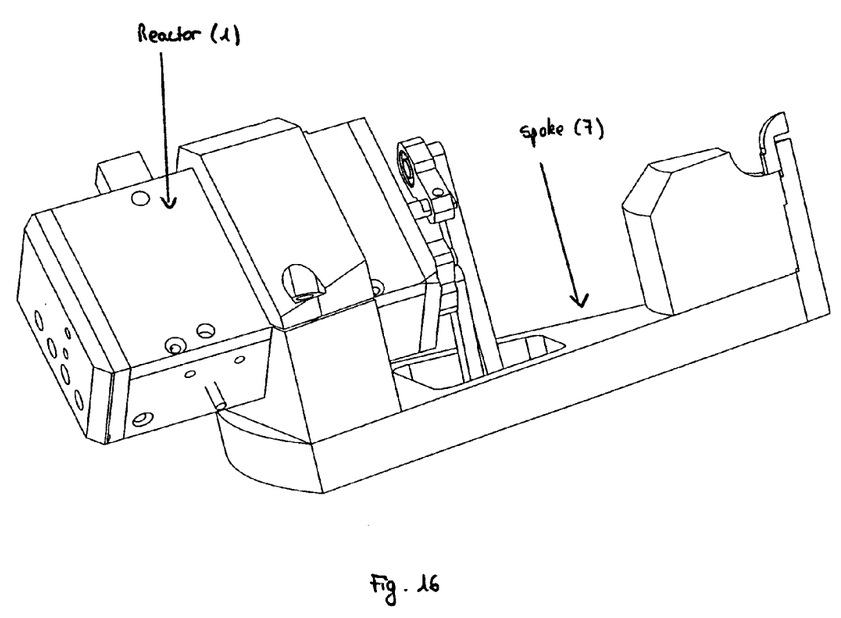
FIG. 16 is a perspective view showing the relationships between a reactor and a spoke.

Turning now to the reactors (1) shown in FIGS. 1 to 3, affixed to the ends of spokes (7) of rotor (8) of centrifuge (9) shown in FIG. 4 are inclined in relation to the vertical passing through the spoke, in a plane passing through this spoke.

The reactors are constituted of three elements:

The body (3) of the reactor which is traversed by spoke (7) of rotor (8). It has a track on one of its two large surfaces. It can have, on the lower part of the exterior surface, an opening blocked by a pressing stopper applied by means of a spring and which by means of centripetal force is moved away from the surface and liberates the opening. It can also have on the same surface another opening blocked by a stopper from the interior and held in position by a spring. It is possible to inject a liquid under pressure into the reactor by applying a telescoping nozzle on this opening.

A biochip-carrier (2) sliding part (4), which when it is furnished with the biochip and engaged at the bottom in its track, blocks one of the two large surfaces of the reactor. The biochip carrier can be moved by about one or about two millimeters in its track, without harming the tightness of the reactor, to improve the contact of the deposits with the reagents. It can be moved away from its original position towards the exterior by about six or about seven millimeters to open the reactor and allow the discharge of its content. Finally, it can be moved away from its original position by several centimeters to be brought out of the centrifuge enclosure and placed in the field of the signal acquisition system. The biochip carriers or, in other cases, the reactors are activated by the mechanical translational movement device mentioned above.

An agitator (5) composed of a blade (6) which can either be supported on the lower part of the biochip forming a solid angle which retains a small volume of liquid, or from this position come to be applied on the biochip spreading over its surface and without air bubble the volume of liquid retained, or enter completely into the body of the reactor to allow the sliding of the biochip carrier.

The continuous passage between these three positions causes the discharge of the washing liquid on the active surface of the biochip.

The rotation of the reactors (1) at slow speed causes the accumulation of the contained liquid towards the exterior. Stopping this rotation cancels such accumulation and creates a reflux of the liquid towards rotor (8). The succession of rotational starts and stops agitates the liquids and accelerates washing of the biochips.

Other types of reactors can be envisaged such as, for example, the three versions of the carrier devices (10) presented in FIGS. 5 and 6, 7 to 9 and 10 and 11. They are simpler and less expensive to manufacture, but they do not allow approaching very close to the active surface of the biochip for acquisition of the signal. In this case, it is the entire reactor which is pushed to the exterior of the centrifuge's enclosure.

The invention claimed is:

1. An automated device for biological analysis comprising:
   a centrifuge comprising a rotatable rotor having spokes; and
   at least one reactor fixed to the spokes, the at least one reactor comprising a body, a biochip carrier and an agitator, the agitator comprising a blade which can take up three positions:
   1) a first position bearing against a lower portion of a biochip carrier formed at an angle to retain a small volume of liquid,
   2) a second position following the first position to apply the liquid on a biochip supported by the biochip carrier such that liquid spreads over a surface of the biochip and without forming an air bubble, and
   3) a third position that enters completely into the body.

2. The automated device according to claim 1, wherein the at least one reactor is affixed to an end portion of one of the spokes and is inclined in relation to a vertical axis passing through the spoke.

3. The automated device according to claim 1, wherein the body has two large surfaces with a track on one of the surfaces, wherein a lower part of one of the surfaces has an opening blocked by a pressing stopper, wherein the pressing stopper is pressed into the opening by the action of a spring, and which by means of centripetal force, is moved away from the surface and opens the opening.

4. The automated device according to claim 3, wherein the surface with the stopper has another opening blocked by a stopper from an interior portion of the body, held in position by a spring to enable injection of a liquid under pressure into the at least one reactor.

5. The automated device according to claim 3, wherein the biochip carrier has a sliding part which, when furnished with the biochip and engaged at a bottom portion of the track, blocks one of the two surfaces of the reactor.

6. The automated device according to claim 5, further comprising a mechanical translational device, making it possible to pull the sliding part to a periphery position and then to return the sliding part to an initial position.

7. The automated device according to claim 6, further comprising a mechanical translational device, making it possible to pull the reactor to a periphery position and then to return the reactor to an initial position.

8. The automated device according to claim 5, further comprising a mechanical translational device, making it possible to pull the reactor to a periphery position and then to return the reactor to an initial position.

9. The automated device according to claim 1, wherein the rotor is driven according to cycles alternating starting and stopping rotational movement to create a reflux of the liquid towards the rotor.

10. The automated device according to claim 9, wherein the nozzles are connected by calibrated catheters to the cover of a hermetic enclosure which comprises a number of tubes containing labeled molecules and means for application of pressure.

11. The automated device according to claim 1, wherein the centrifuge is equipped with a cover provided with fixed nozzles spaced apart in a substantially regular manner and equal in number to the number of reactors of the rotor and located on a circumference whose radius is substantially equal to that of the center of the reactors.

12. The automated device according to claim 11, wherein the cover further comprises nozzles for distribution of reagents into each reactor.

13. The automated device according to claim 11, wherein the cover further comprises nozzles for discharging liquids for cleaning and decontamination of the device.

14. The automated device according to claim 13, wherein the agitator moves between the three positions in a continuous manner.

* * * * *